US009360418B2

(12) United States Patent  (10) Patent No.: US 9,360,418 B2
Georgeson  (45) Date of Patent: Jun. 7, 2016

(54) NONDESTRUCTIVE INSPECTION USING HYPERSOUND

(71) Applicant: The Boeing Company, Chicago, IL (US)

(72) Inventor: Gary Ernest Georgeson, Tacoma, WA (US)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 14/333,799

(22) Filed: Jul. 17, 2014

(65) Prior Publication Data

US 2016/0018324 A1  Jan. 21, 2016

(51) Int. Cl.
| | |
|---|---|
| *G01N 21/3563* | (2014.01) |
| *G01N 29/04* | (2006.01) |
| *G01N 29/12* | (2006.01) |
| *G01N 29/24* | (2006.01) |
| *G01N 21/17* | (2006.01) |
| *G01N 21/70* | (2006.01) |

(52) U.S. Cl.
CPC ........ *G01N 21/3563* (2013.01); *G01N 21/1702* (2013.01); *G01N 21/70* (2013.01); *G01N 29/04* (2013.01); *G01N 29/043* (2013.01); *G01N 29/12* (2013.01); *G01N 29/2418* (2013.01); *G01N 29/2431* (2013.01)

(58) Field of Classification Search
CPC ........ G01J 5/02; G01N 29/22; G01N 21/3563
See application file for complete search history.

(56) References Cited

U.S. PATENT DOCUMENTS

| | | | | |
|---|---|---|---|---|
| 6,087,652 | A * | 7/2000 | O'Meara et al. | ............ 250/214.1 |
| 6,092,419 | A | 7/2000 | Dixon et al. | |
| 6,397,680 | B1 | 6/2002 | Levesque et al. | |
| 7,287,902 | B2 * | 10/2007 | Safai et al. | ................. 374/5 |
| 2004/0089812 | A1 * | 5/2004 | Favro | ...................... G01N 3/60 |
| | | | | 250/341.6 |
| 2008/0217536 | A1 * | 9/2008 | Sekiguchi | .............. G01V 8/005 |
| | | | | 250/334 |
| 2008/0245964 | A1 * | 10/2008 | Miles | ..................... G01N 22/00 |
| | | | | 250/288 |
| 2012/0320383 | A1 | 12/2012 | Dubois et al. | |

FOREIGN PATENT DOCUMENTS

| | | |
|---|---|---|
| EP | 2518480 A1 | 10/2012 |
| WO | WO9944051 A1 | 9/1999 |

OTHER PUBLICATIONS

Adams, "Nonlinear Dynamics . . . to see what is unseen in lightweight blades," Vanderbilt University, Laboratory for Systems Integrity & Reliability, Nov. 2013, 37 pages.

(Continued)

*Primary Examiner* — David Porta
*Assistant Examiner* — Faye Boosalis
(74) *Attorney, Agent, or Firm* — Yee & Associates, P.C.

(57) ABSTRACT

A method and apparatus for inspecting an object. The apparatus comprises a wave generator and a detection system. The wave generator is positioned away from an object. The wave generator emits an ultrasonic wave in a direction towards a location on the object such that the ultrasonic wave encounters a portion of the object. The detection system is positioned at a same side of the object as the wave generator. The detection system detects a feature response of a feature within the portion of the object to the ultrasonic wave encountering the portion of the object.

20 Claims, 10 Drawing Sheets

(56) References Cited

OTHER PUBLICATIONS

Solodov, "Resonance of defects: an advance toward efficient nonlinear ultrasonic NDE and ultrasonic thermography," University of Stuttgart, Dresden Airport Seminar, Nov. 2013, 35 pages.

Tapia et al., "Non-Destructive Evaluation of Structures Using Motion Magnification Technology," U.S. Appl. No. 14/165,676, filed Jan. 28, 2014, 28 pages.

Extended European Search Report, dated Nov. 11, 2015, regarding Application No. EP15176314.1, 6 pages.

* cited by examiner

NONDESTRUCTIVE INSPECTION USING HYPERSOUND

BACKGROUND INFORMATION

1. Field

The present disclosure relates generally to inspection systems and, in particular, to nondestructive inspection systems. Still more particularly, the present disclosure relates to a method and apparatus for nondestructively inspecting an object for features of interest using hypersound.

2. Background

Nondestructive inspection (NDI) systems are oftentimes used to inspect different types of objects. Nondestructive inspection systems allow an object, such as an aircraft structure, to be inspected without affecting the object in an undesired manner. In some cases, a nondestructive system may also be referred to as a nondestructive testing (NDT) system or a nondestructive evaluation (NDE) system.

Some currently available methods for performing nondestructive inspection require that one or more components of the nondestructive inspection system be in physical contact with the object being inspected. However, these types of physical contact-based nondestructive inspection methods may be more time-consuming, labor-intensive, and expensive than desired. Further, some of these physical contact-based nondestructive inspection methods may pose safety issues for the personnel needed to operate the nondestructive inspection systems being used. Still further, direct access to the object needed for some of the physical contact-based nondestructive inspection methods may not be possible with certain types of objects.

One solution is to use "stand-off" nondestructive inspection methods in which the nondestructive inspection system is positioned away from the object being inspected such that the nondestructive inspection system does not physically contact the object. However, some of the currently available stand-off nondestructive inspection methods may be more expensive than desired, may not easily be made portable, and may require physically impacting the object in a manner that causes undesired features to form on the surface of the object. Therefore, it would be desirable to have a method and apparatus for performing nondestructive inspection that take into account at least some of the issues discussed above, as well as other possible issues.

SUMMARY

In one illustrative embodiment, an apparatus comprises a wave generator and a detection system. The wave generator is positioned away from an object. The wave generator emits an ultrasonic wave in a direction towards a location on the object such that the ultrasonic wave encounters a portion of the object. The detection system is positioned at a same side of the object as the wave generator. The detection system detects a feature response of a feature within the portion of the object to the ultrasonic wave encountering the portion of the object.

In another illustrative embodiment, a nondestructive inspection system comprises a wave generator, a detection system, and a controller. The wave generator is positioned away from an object such that the wave generator is not in direct physical contact with the object. The wave generator emits a hypersonic wave in a direction towards a location on the object such that the hypersonic wave encounters a portion of the object. The detection system is positioned at a same side of the object as the wave generator. The detection system detects a response of the portion of the object to the hypersonic wave encountering the portion of the object. The response includes a feature response that is produced when a feature that is present within the portion of the object has an amplified vibration relative to a rest of the portion of the object in response to the hypersonic wave encountering the portion of the object. The controller controls a frequency at which the hypersonic wave is emitted.

In yet another illustrative embodiment, a method for inspecting an object is provided. A wave generator is positioned away from the object. An ultrasonic wave is emitted from the wave generator in a direction towards a location on the object such that the ultrasonic wave encounters a portion of the object. A feature response of a feature within the portion of the object to the ultrasonic wave encountering the portion of the object is detected using a detection system positioned at a same side of the object as the wave generator.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative embodiments recognize and take into account different considerations. In particular, the illustrative embodiments recognize and take into account that performing nondestructive inspection using hypersonic waves may allow the wave generator in the nondestructive inspection system generating the hypersonic waves to be positioned away from the object being inspected such that the wave generator is not in direct physical contact with the object. For example, the wave generator may be positioned two inches, one foot, five feet, twenty feet, fifty feet, or some other distance away from the object.

The illustrative embodiments also recognize and take into account that using this type of nondestructive inspection system may allow inspections to be performed more quickly, while maintaining accuracy of the results of the inspection. Further, using this type of nondestructive inspection system reduces the potential for causing undesired effects to the object being inspected.

Thus, the illustrative embodiments provide a method, apparatus, and system for performing nondestructive inspection of an object. As one illustrative example, a wave generator may be positioned away from the object such that the wave generator is not in direct physical contact with the object. An ultrasonic wave may then be emitted from the wave generator in a direction towards a location on the object such that the ultrasonic wave encounters the object. The location may be a portion of the object. This portion may be a section of the object, a piece of the object, a part of the object, or some other portion of the object.

A response of the portion of the object to the ultrasonic wave encountering the portion of the object may be detected using a detection system positioned at a same side of the object as the wave generator. An image of the portion of the object may then be generated based on the response detected. This image may be used to determine whether a feature is present within the portion of the object. The feature may be, for example, without limitation, an undesired feature such as a flaw. In some cases, the image may be used to identify information about the feature.

Figure 1:
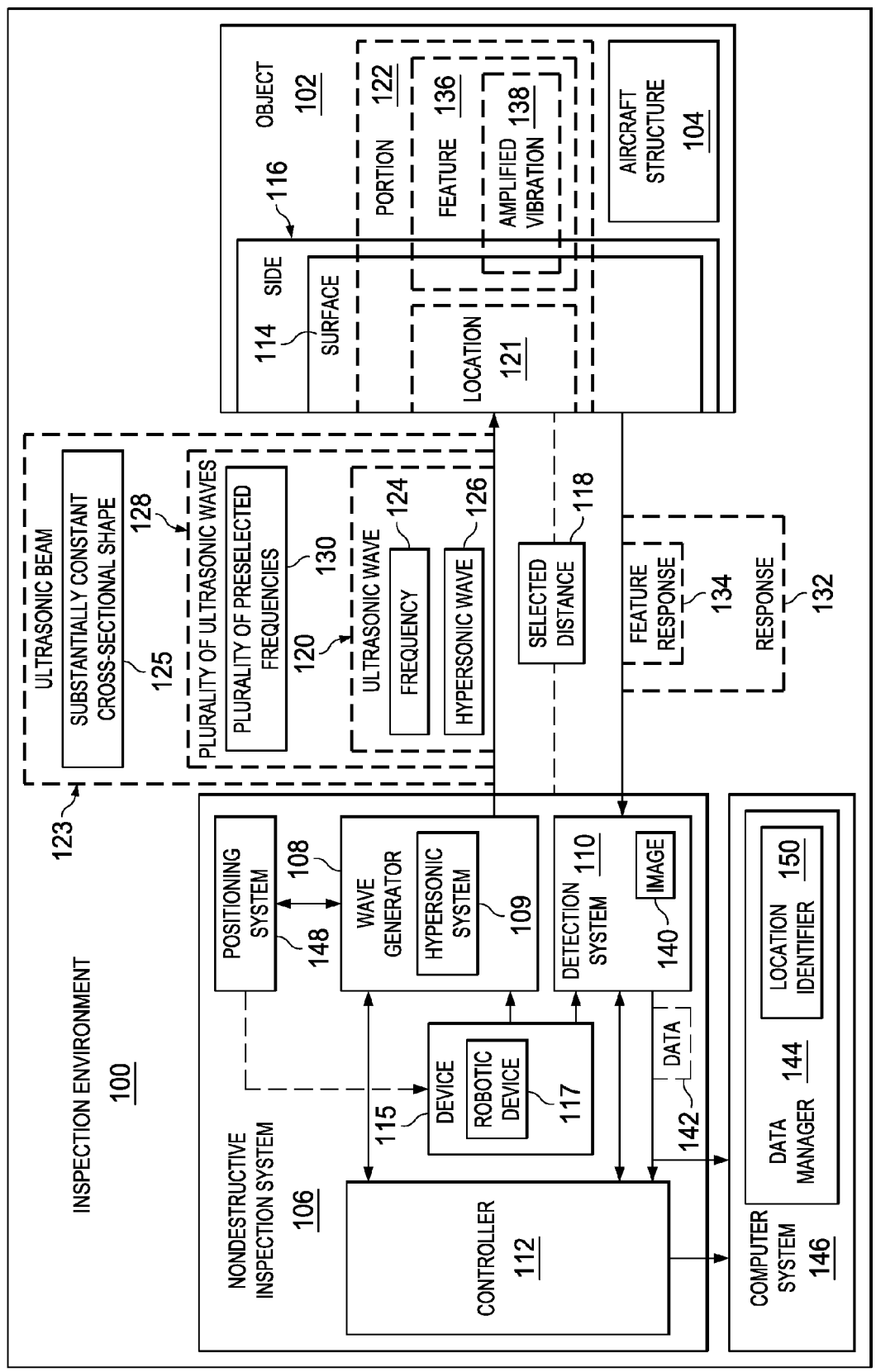
FIG. 1 is an illustration of an inspection environment in the form of a block diagram in accordance with an illustrative embodiment.

Referring now to the figures and, in particular, with reference to FIG. 1, an illustration of an inspection environment is depicted in the form of a block diagram in accordance with an illustrative embodiment. In this illustrative example, inspection environment 100 is any environment in which an object, such as object 102, may be inspected.

Object 102 may take a number of different forms. In one illustrative example, object 102 takes the form of aircraft structure 104. Aircraft structure 104 may be, for example, without limitation, a fuselage of an aircraft, a wing of an aircraft, a spar, a rib, a skin panel, an aileron, a flap, a stabilizer, or some other type of structure in an aircraft. In other illustrative examples, object 102 may take the form of a door, a wall, or some other type of structure.

Object 102 may take the form of a composite object in this illustrative example. In other words, object 102 may be comprised of one or more layers of composite material. In other illustrative examples, object 102 may take the form of a non-composite object or a partially composite object. For example, object 102 may be comprised of a composite material, metal, a metal alloy, a plastic material, one or more other types of material, or some combination thereof.

As depicted, nondestructive inspection system 106 may be used to inspect object 102. In particular, nondestructive inspection system 106 may be used to inspect object 102 to determine whether one or more features of interest are present in object 102. In some illustrative examples, the feature of interest may be, for example, without limitation, an undesired feature. As used herein, an "undesired feature" may be any inconsistency in object 102 that is undesired. For example, an undesired feature may be a disbond, a crack, a micro-crack, a delamination, a wrinkle, foreign object debris (FOD), a void, an undesired porosity, or some other type of feature that is not desirable for object 102. A disbond may be a bond that has been weakened such that a strength of the bond is below some selected threshold. Nondestructive inspection system 106 includes wave generator 108, detection system 110, and controller 112. Wave generator 108 is configured to be positioned away from surface 114 at side 116 of object 102. In particular, wave generator 108 may be positioned at selected distance 118 away from surface 114 at side 116 of object 102. Selected distance 118 may be, for example, but not limited to, at least two inches away from surface 114 at side 116 of object 102.

In some illustrative examples, device 115 may be used to position wave generator 108 at selected distance 118 away from surface 114. Wave generator 108 may be associated with device 115. As used herein, when one component is "associated" with another component, the association is a physical association in the depicted examples.

For example, a first component, such as wave generator 108, may be considered to be associated with a second component, such as device 115, by being at least one of secured to the second component, bonded to the second component, mounted to the second component, welded to the second component, adhered to the second component, fastened to the second component, or connected to the second component in some other suitable manner. The first component also may be connected to the second component using a third component. Further, the first component may be considered to be associated with the second component by being formed as part of the second component, an extension of the second component, or both.

As used herein, the phrase "at least one of," when used with a list of items, means different combinations of one or more of the listed items may be used and only one of the items in the list may be needed. The item may be a particular object, thing, action, process, or category. In other words, "at least one of" means any combination of items or number of items may be used from the list, but not all of the items in the list may be required.

For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

In one illustrative example, device 115 may take the form of a tripod or some other type of mounting structure. In other illustrative examples, device 115 may take the form of robotic device 117. Robotic device 117 may be implemented in the form of, for example, without limitation, a robotic arm.

Wave generator 108 is configured to generate ultrasonic wave 120. With wave generator 108 positioned at selected distance 118 away from surface 114, wave generator 108 may emit ultrasonic wave 120 towards location 121 on object 102. In one illustrative example, location 121 may be a point on object 102 in two dimensions or three dimensions. In other illustrative examples, location 121 may be an area on surface 114 of object 102. Depending on the size and shape of object 102, location 121 may be an area corresponding to the entirety of object 102.

In this illustrative example, ultrasonic wave 120 may be directed towards location 121 on object 102 such that ultrasonic wave 120 encounters portion 122 of object 102. Portion 122 of object 102 may be some or all of object 102 at and around location 121. For example, portion 122 may be a section of object 102, a piece of object 102, a part of object 102, or some other portion of object 102.

Wave generator 108 emits ultrasonic wave 120 in a manner that reduces the spreading of ultrasonic wave 120 as ultrasonic wave 120 travels towards location 121 on object 102. In particular, wave generator 108 focuses ultrasonic wave 120 in the form of a highly directional ultrasonic beam 123 such that the spreading of ultrasonic wave 120 is reduced during propagation. Reducing the spreading of ultrasonic wave 120 reduces energy loss as ultrasonic wave 120 travels towards location 121 on object 102.

As depicted, wave generator 108 emits ultrasonic wave 120 in a particular direction towards location 121 on object 102 with reduced spreading such that ultrasonic beam 123 is formed. Ultrasonic beam 123 may be formed such that ultrasonic beam 123 is substantially cylindrical in shape. For example, ultrasonic beam 123 may have substantially constant cross-sectional shape 125. The energy of ultrasonic wave 120 may be considered substantially constrained within the path along which ultrasonic beam 123 is formed.

Ultrasonic wave 120 may have frequency 124. Controller 112 may control frequency 124 of ultrasonic wave 120. Frequency 124 is selected such that any features of interest in portion 122 of object 102 will vibrate in a particular manner relative to a rest of portion 122 of object 102. As one illustrative example, controller 112 may control the operation of wave generator 108 such that frequency 124 of ultrasonic wave 120 is between about 1 kilohertz and about 500 kilohertz.

When ultrasonic beam 123 has substantially constant cross-sectional shape 125 and has ultrasonic wave 120 with frequency 124 between about 1 kilohertz and about 500 kilohertz, ultrasonic beam 123 may be referred to as a hypersonic beam. In particular, ultrasonic wave 120 may be referred to as hypersonic wave 126. Wave generator 108 may take the form of any type of hypersonic system 109 capable of generating hypersonic wave 126 having frequency 124 between about 1 kilohertz and about 500 kilohertz in the form of ultrasonic beam 123 having substantially constant cross-sectional shape 125.

Hypersonic system 109 may be implemented using, for example, without limitation, HyperSound™ technology, provided by the Turtle Beach Corporation. HyperSound™ technology may allow a directional and narrow ultrasonic beam 123 to be generated such that a precise ultrasonic, or hypersonic, zone is created. With this type of technology, ultrasonic beam 123 may be precisely directed at location 121 on object 102 even when hypersonic system 109 is positioned away from object 102 at distances from object 102 greater than many feet. Thus, nondestructive inspection system 106 may be used to perform "standoff" nondestructive inspection at distances such as, for example, without limitation, two inches, ten inches, two feet, five feet, twenty feet, seventy-five feet, or some other distance from object 102.

In some illustrative examples, ultrasonic wave 120 may be one of plurality of ultrasonic waves 128 that are emitted towards portion 122 of object 102. Plurality of ultrasonic waves 128 may be emitted at plurality of preselected frequencies 130. In particular, each of plurality of ultrasonic waves 128 may be emitted at a corresponding one of plurality of preselected frequencies 130.

Plurality of preselected frequencies 130 may be selected such that emitting plurality of ultrasonic waves 128 towards portion 122 of object 102 performs a frequency sweep of portion 122 of object 102. In one illustrative example, plurality of preselected frequencies 130 may be selected based on test results obtained using a reference object. This reference object is sometimes referred to as a reference standard or a standard.

For example, a reference object having a known undesired feature may be tested using nondestructive inspection system 106. One or more particular frequencies at which the known undesired feature vibrates in a manner that can be distinguished from the vibration of the rest of the reference objects are identified. These one or more particular frequencies are then used to select plurality of preselected frequencies 130.

In one illustrative example, plurality of preselected frequencies 130 may be selected as a frequency range that includes the one or more particular frequencies. For example, the frequency range may be swept through a continuous range, such as from about 10 kilohertz to about 200 kilohertz. In another example, the frequency range may be a broad band of a continuous frequency range for an ultrasonic pulse. This frequency range may be, for example, without limitation, between about 5 kilohertz and about 25 kilohertz, between about 20 kilohertz and about 40 kilohertz, or between some other range of frequencies in kilohertz. In another example, the frequency range may be a discontinuous range that includes the frequencies at some selected interval from about 10 kilohertz to about 200 kilohertz. For example, the frequency at every 10 kilohertz, 20 kilohertz, 50 kilohertz, or some other selected interval within a particular range, may be included.

Ultrasonic wave 120 may travel through one or more fluids over selected distance 118 until ultrasonic wave 120 encounters surface 114 of portion 122 of object 102. As used herein, a "fluid" may be comprised of any number of gases, any number of liquids, or some combination thereof. For example, without limitation, the fluid may be air, water, or a combination of the two. As one illustrative example, ultrasonic wave 120 may travel through water when, for example, without limitation, nondestructive inspection system 106 is used to perform nondestructive inspection underwater. In these illustrative examples, ultrasonic wave 120 may travel through a number of fluids until ultrasonic wave 120 encounters surface 114 of portion 122 of object 102 without requiring a separate, additional coupling medium or coupling element.

When ultrasonic wave 120 encounters surface 114 of portion 122 of object 102, at least portion 122 of object 102 vibrates. Detection system 110 is used to detect response 132 of portion 122 of object 102 to ultrasonic wave 120 encountering surface 114 of portion 122 of object 102. As depicted, detection system 110 is positioned at the same side 116 of object 102 as wave generator 108.

Depending on the implementation, detection system 110 may be associated with at least one of wave generator 108 or device 115. Examples of different implementations for detection system 110 are described with respect to FIG. 2 below.

Response 132 is the vibratory response of portion 122 of object 102. When a feature of interest, such as feature 136, is present within portion 122, response 132 may include feature response 134. Feature 136 may be, for example, a particular layer in object 102, a part that has been bonded to object 102, a membrane, one or more characteristics of a bond, a number of dimensions of a bond, a layer in object 102 having a thickness below a selected threshold, a particular structural pattern, or some other type of feature of interest. In some illustrative examples, feature 136 may be an undesired feature such as, but not limited to, a disbond, a crack, a micro-crack, a delamination, a wrinkle, foreign object debris (FOD), a void, an undesired porosity, or some other type of feature that is not desirable for object 102.

Feature response 134 may be a portion of response 132 that is different and thus, distinguishable, from a rest of response 132. In some cases, ultrasonic wave 120 may be directed at the entirety of object 102. In these cases, response 132 may be the response of the entirety of object 102, which includes portion 122 of object 102, and feature response 134 of feature 136 within portion 122 may be the portion of response 132 that is distinguishable from a rest of response 132.

In one illustrative example, feature response 134 may be produced when feature 136 within portion 122 of object 102 has amplified vibration 138 relative to a rest of portion 122 of object 102 in response to ultrasonic wave 120 encountering surface 114 of portion 122. Amplified vibration 138 may be vibration of feature 136 with greater amplitude than the vibration of the rest of portion 122. In some illustrative examples, amplified vibration 138 may be vibration having amplitude above a selected threshold.

In other illustrative examples, amplified vibration 138 may take the form of resonance. For example, without limitation, when ultrasonic wave 120 has frequency 124 that is substantially equal to or within a selected range of the natural frequency of feature 136, feature 136 may vibrate with increased amplitude relative to a rest of portion 122 of object 102 in response to ultrasonic wave 120 impinging upon surface 114 of portion 122 of object 102. This type of amplified vibration of feature 136 may be referred to as resonance. In this manner, feature response 134 may be distinguishable from a rest of response 132. The natural frequency of feature 136 is the frequency at which feature 136 tends to oscillate in the absence of any driving or damping forces. The natural frequency of feature 136 may be different from the natural frequency of object 102.

In this illustrative example, amplified vibration 138 may be detected as feature response 134 within response 132 when feature response 134 has a value for some measurable parameter greater than some selected threshold relative to a rest of response 132. For example, without limitation, heat generated by the vibration of portion 122 of object 102 may be measured. Feature response 134 may be detected when the heat measured for one portion of response 132 is greater than some selected threshold relative to a rest of response 132. Detecting feature response 134 indicates the presence of feature 136 within portion 122 of object 102.

Depending on the implementation, feature response 134 may only be detectable when ultrasonic wave 120 has frequency 124 within a selected range of the natural frequency of feature 136. This selected range may be, for example, but is not limited to, within about fifty hertz, about one hundred hertz, about one kilohertz, about two kilohertz, five kilohertz, or about eight kilohertz of the natural frequency. The selected range may be up to about ten kilohertz off of the natural frequency in some cases.

In this illustrative example, detection system 110 generates image 140 based on response 132. When response 132 includes feature response 134, image 140 may include a visual representation of feature 136. For example, image 140 may include an outline of feature 136.

In some cases, more than one feature of interest may be present within portion 122 of object 102. Detection system 110 may be capable of detecting the feature responses of these multiple features of interest. Depending on the size, shape, and type of the features of interest, different features of interest may result in feature responses at different frequencies of ultrasonic wave 120.

Some features of interest may result in feature responses at substantially the same frequencies. In these cases, image 140 may include a visual representation of these features of interest.

In some illustrative examples, image 140 may be sent as part of data 142 to data manager 144 for processing. Data manager 144 may at least one of analyze data 142, store data 142, generate a report using data 142, or perform other actions using data 142.

Data manager 144 may be implemented using hardware, firmware, software, or some combination thereof. In this illustrative example, data manager 144 may be implemented using computer system 146. Computer system 146 may be comprised of one or more computers in communication with each other. In other illustrative examples, data manager 144 or at least a portion of data manager 144 may be implemented within controller 112.

Controller 112 may also be implemented using hardware, firmware, software, or some combination thereof. For example, controller 112 may be implemented using a computer, a processor unit, a microprocessor, a microchip, an integrated circuit, or some combination thereof. In some cases, controller 112 may be implemented as part of wave generator 108.

In some illustrative examples, controller 112 may be used to control the operation of detection system 110, device 115 used for positioning wave generator 108, or both. For example, when device 115 takes the form of robotic device 117, controller 112 may send commands to robotic device 117 to control operation of robotic device 117.

In one illustrative example, nondestructive inspection system 106 may include positioning system 148. Positioning system 148 may be associated with wave generator 108. Positioning system 148 may be comprised of one or more sensor devices configured to generate sensor data about the position of wave generator 108 relative to object 102. For example, positioning system 148 may generate sensor data that identifies a location of portion 122 on object 102 towards which ultrasonic wave 120 is emitted.

Depending on the implementation, positioning system 148 may be implemented as part of device 115 or independently of device 115. For example, device 115 may include positioning system 148 and may use the sensor data generated by positioning system 148 to position wave generator 108, detection system 110, or both relative to object 102 such that ultrasonic beam 123 may be precisely positioned. When object 102 takes the form of aircraft structure 104, positioning system 148 may take the form of a local positioning system configured to position wave generator 108, detection system 110, or both with respect to a reference coordinate system for aircraft structure 104 or the aircraft to which aircraft structure 104 belongs.

Data manager 144 may include location identifier 150. Location identifier 150 may use at least one of image 140, sensor data received from positioning system 148, a reference coordinate system for object 102, or other information to identify a location of feature 136 with respect to a coordinate system for object 102.

Figure 2:
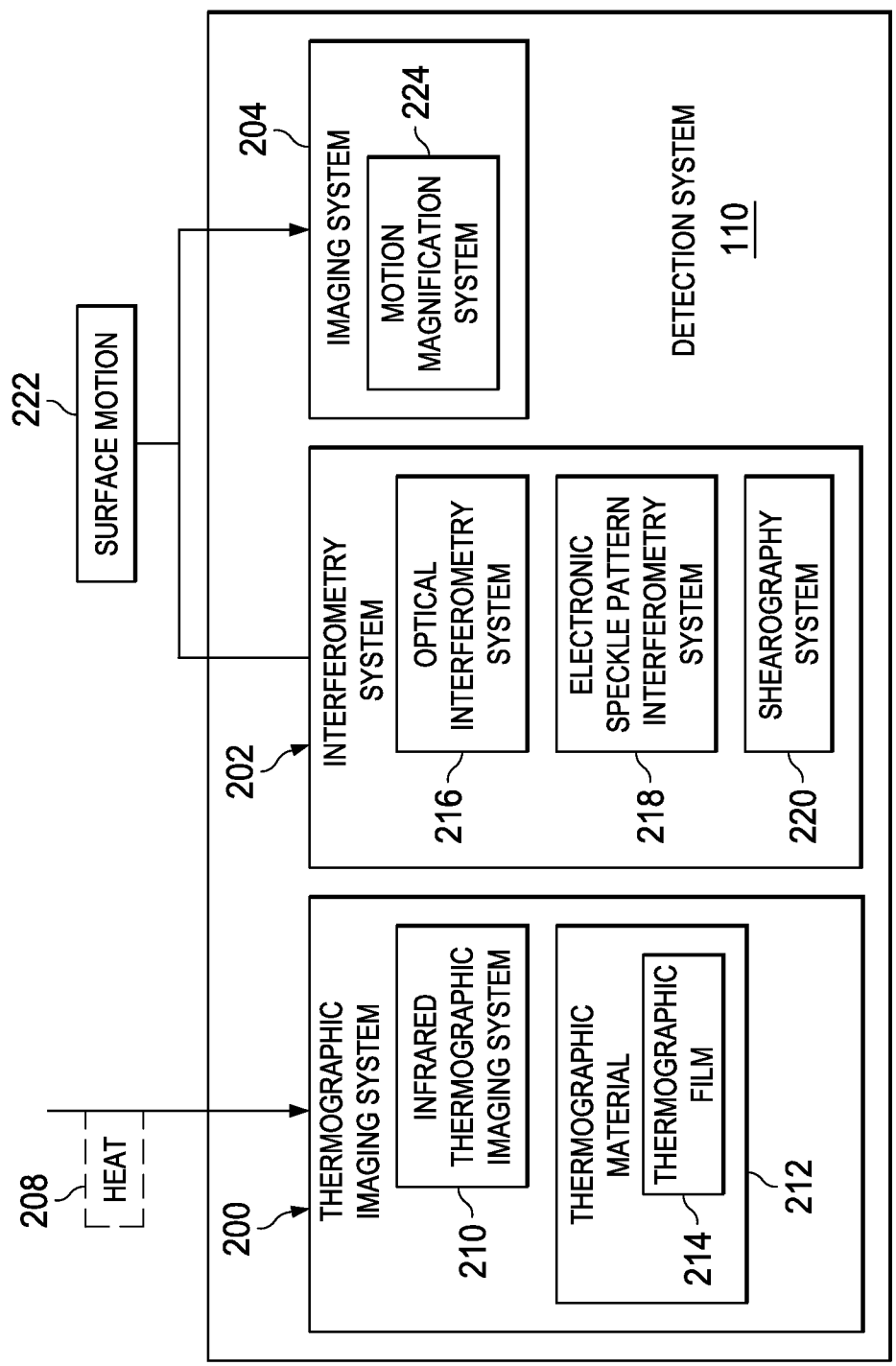
FIG. 2 is an illustration of a detection system in the form of a block diagram in accordance with an illustrative embodiment.

With reference now to FIG. 2, an illustration of detection system 110 from FIG. 1 is depicted in the form of a block diagram in accordance with an illustrative embodiment. Depending on the implementation, detection system 110 may include one or more imaging systems that detect the feature response and convert it into an image.

Heat 208 may be an example of one measurable parameter that detection system 110 may use to detect response 132 in FIG. 1. Heat 208 may be generated in response to vibration of portion 122 of object 102 in FIG. 1. For example, without limitation, the vibration, or oscillation, of portion 122 of object 102 may cause different areas on surface 114 of object 102 in FIG. 1 to come into contact with each other and move relative to each other, while these areas are in contact with each other. The friction created between these areas of surface 114 moving relative to each other while in contact with each other may convert kinetic energy into heat 208 that may be detectable.

Heat 208 generated by amplified vibration 138 of feature 136 may be greater than heat 208 generated by a rest of portion 122 of object 102. Consequently, heat 208 generated by amplified vibration 138 of feature 136 may be distinguishable as feature response 134 in FIG. 1.

In this illustrative example, detection system 110 may include at least one of thermographic imaging system 200, interferometry system 202, or imaging system 204. Thermographic imaging system 200 is configured to detect heat 208 generated by amplified vibration 138 of feature 136 in FIG. 1 and to generate image 140 shown in FIG. 1 based on heat 208 detected.

Thermographic imaging system 200 may take a number of different forms. In one illustrative example, thermographic imaging system 200 takes the form of infrared thermographic imaging system 210. Infrared thermographic imaging system 210 detects heat 208 in the form of infrared radiation. For example, infrared thermographic imaging system 210 may detect the infrared radiation generated by amplified vibration 138 of feature 136 and generates image 140 of feature 136 based on the infrared radiation detected.

In another illustrative example, thermographic imaging system 200 takes the form of thermographic material 212. Thermographic material 212 may be positioned relative to surface 114 of portion 122 of object 102. Thermographic material 212 is configured to generate a visual representation of feature 136 on a portion of thermographic material 212 in response to detecting heat 208 generated by amplified vibration 138 of feature 136. Thermographic material 212 may take the form of thermographic film 214 in some cases.

Surface motion 222 may be another example of one measurable parameter that detection system 110 may use to detect response 132 in FIG. 1. When portion 122 of object 102 vibrates, surface 114 of portion 122 of object 102 may be displaced in an oscillating manner. The motion of surface 114 may be detected as surface motion 222. Thus, while the vibration of portion 122 of object 102 in response to ultrasonic wave 120 impinging surface 114 of object 102 may include vibration of portion 122 up to some thickness beneath surface 114, only surface motion 222 may be detectable.

Surface motion 222 of surface 114 corresponding to, or co-located with, feature 136 may be greater than surface motion 222 by surface 114 of a rest of portion 122 of object 102. Consequently, surface motion 222 generated by amplified vibration 138 of feature 136 may be distinguishable as feature response 134.

Interferometry system 202 may take the form of optical interferometry system 216, electronic speckle pattern interferometry system 218, shearography system 220, or some other type of interferometry system. Interferometry system 202 uses surface motion 222 of portion 122 of object 102 in FIG. 1 produced by object 102 vibrating in response to ultrasonic wave 120 impinging upon surface 114 of portion 122 in FIG. 1 to generate image 140.

Imaging system 204 may be yet another example of one implementation for detection system 110. Imaging system 204 is configured to detect surface motion 222 and magnify surface motion 222 to generate image 140. In some illustrative examples, imaging system 204 may be referred to as motion magnification system 224.

In other illustrative examples, detection system 110 may include some other type of imaging system. For example, detection system 110 may include an imaging system capable of detecting both heat 208 and surface motion 222. Detection system 110 may include any imaging system capable of detecting response 132 in FIG. 1 and converting response 132 into image 140.

The illustrations of inspection environment 100 in FIG. 1 and detection system 110 in FIGS. 1-2 are not meant to imply physical or architectural limitations to the manner in which an illustrative embodiment may be implemented. Other components in addition to or in place of the ones illustrated may be used. Some components may be optional. Also, the blocks are presented to illustrate some functional components. One or more of these blocks may be combined, divided, or combined and divided into different blocks when implemented in an illustrative embodiment.

For example, in some cases, positioning system 148 may not be used. In some illustrative examples, computer system 146 may be located remotely with respect to nondestructive inspection system 106. In this manner, data 142 may be analyzed in a different location than inspection environment 100. In other illustrative examples, other implementations for detection system 110 may be used in place of the ones shown in FIG. 2.

In still other illustrative examples, location identifier 150 may be implemented remotely. For example, location identifier 150 may be implemented in another computer system in a location outside of inspection environment 100. This other computer system may be in communication with at least one of data manager 144 through computer system 146, controller 112, or positioning system 148.

In some illustrative examples, detection system 110 may not include an imaging system. For example, detection system 110 may be configured to generate data 142 about response 132 that may be sent to controller 112, data manager 144, or both. In this example, data 142 may include measurements of heat 208, measurements of surface motion 222, or both for different locations within portion 122 of object 102. For example, detection system 110 may perform a point-by-point measurement of heat 208, surface motion 222, or both for portion 122 of object 102 to generate data 142. Data 142 may then be processed and analyzed to determine whether feature 136 is present within portion 122 of object 102.

Figure 3:
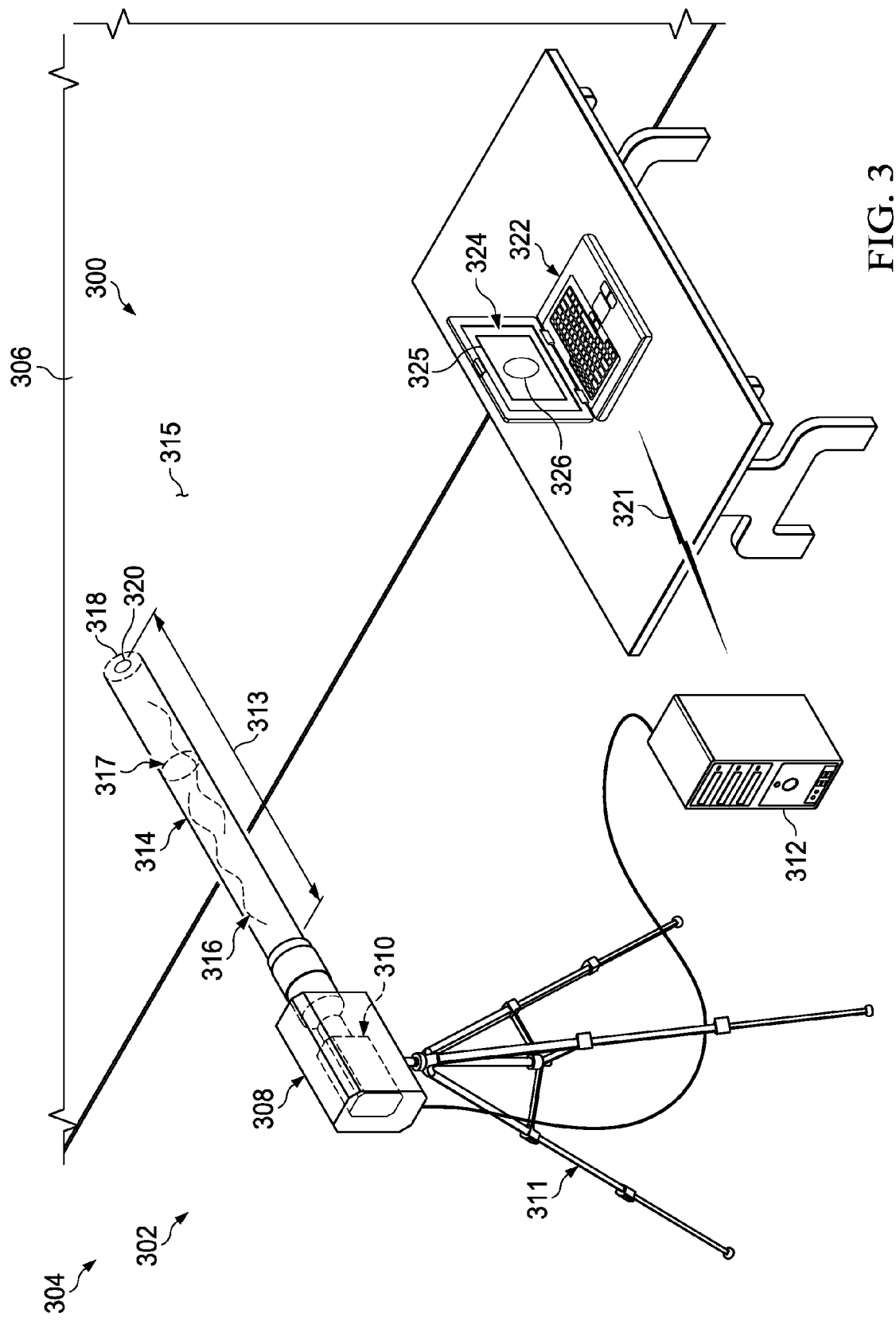
FIG. 3 is an illustration of an inspection environment in accordance with an illustrative embodiment.

With reference now to FIG. 3, an illustration of an inspection environment is depicted in accordance with an illustrative embodiment. In this illustrative example, inspection environment 300 may be an example of one implementation for inspection environment 100 in FIG. 1.

In inspection environment 300, nondestructive inspection system 302 is used to inspect aircraft structure 304. Aircraft structure 304 is an example of one implementation for aircraft structure 104 in FIG. 1. In this illustrative example, aircraft structure 304 is fuselage 306.

Nondestructive inspection system 302 is an example of one implementation for nondestructive inspection system 106 in FIG. 1. Nondestructive inspection system 302 includes wave generator 308, detection system 310, and controller 312, which may be examples of implementations for wave generator 108, detection system 110, and controller 112, respectively, in FIG. 1.

Wave generator 308 and detection system 310 are associated with mounting structure 311. Mounting structure 311 takes the form of a tripod in this illustrative example. Mounting structure 311 is an example of one implementation for device 115 in FIG. 1. Wave generator 308 and detection system 310 are positioned at selected distance 313 away from surface 315 of fuselage 306.

Wave generator 308 is a hypersonic wave generator in this illustrative example. Wave generator 308 emits ultrasonic beam 314 that includes plurality of ultrasonic waves 316. As depicted, ultrasonic beam 314 has substantially constant cross-sectional shape 317. In particular, wave generator 308 directs ultrasonic beam 314 towards portion 318 of fuselage 306. Plurality of ultrasonic waves 316 may be emitted at a plurality of preselected frequencies in succession to perform a frequency sweep of portion 318. Controller 312 controls operation of wave generator 308 such that plurality of ultrasonic waves 316 are emitted at the plurality of preselected frequencies in the form of ultrasonic beam 314.

In some illustrative examples, plurality of ultrasonic waves 316 may be considered as forming a single ultrasonic beam 314 for which the frequency of ultrasonic beam 314 is varied across plurality of preselected frequencies. For example, wave generator 308 may be tuned by controller 312 to change the frequency at which ultrasonic beam 314 is emitted such that ultrasonic beam 314 is emitted at the plurality of preselected frequencies. In other illustrative examples, ultrasonic beam 314 may be formed using a single ultrasonic wave for which a frequency is changed to be each of the plurality of preselected frequencies.

As depicted, undesired feature 320 may be present within portion 318 of fuselage 306. In response to plurality of ultrasonic waves 316 in ultrasonic beam 314 impinging upon surface 315 on portion 318 of fuselage 306, portion 318 of fuselage 306 vibrates. When an ultrasonic wave having a frequency substantially equal to or within a selected range of the natural frequency of undesired feature 320 encounters surface 315, the vibration of undesired feature 320 is amplified relative to the vibration of the rest of portion 318.

Detection system 310 detects the vibratory response of portion 318. In particular, detection system 310 detects the amplified vibration of undesired feature 320. In this illustrative example, detection system 310 may take the form of a thermographic imaging system, such as thermographic imaging system 200 in FIG. 2. Detection system 310 detects the heat generated by the amplified vibration of undesired feature 320 and generates an image based on the heat detected. This image may be sent to controller 312.

Controller 312 may then send the image to computer 322 over wireless communications link 321. Computer 322 may visually present display 325 of the image on screen 324. As depicted, outline 326 of undesired feature 320 may be visually presented in display 325.

Figure 4:
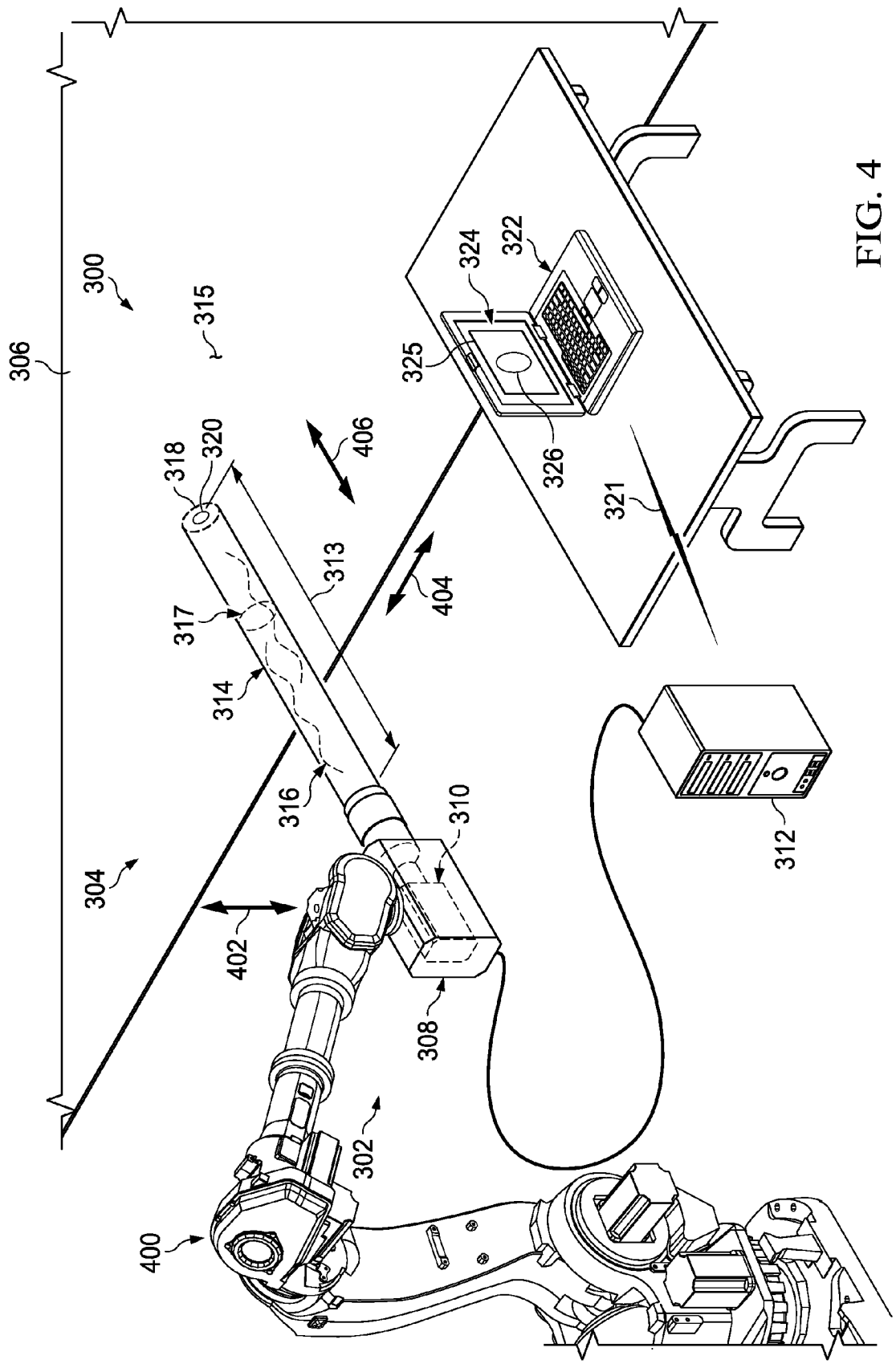
FIG. 4 is an illustration of a different device being used to position a wave generator and a detection system in accordance with an illustrative embodiment.

With reference now to FIG. 4, an illustration of a different device being used to position wave generator 308 and detection system 310 from FIG. 3 is depicted in accordance with an illustrative embodiment. In this illustrative example, robotic arm 400 is used to position wave generator 308 and detection system 310 relative to fuselage 306. Robotic arm 400 is an example of one implementation for robotic device 117 in FIG. 1.

Robotic arm 400 may be used to move wave generator 308 and detection system 310 translationally in directions substantially parallel to axis 402, axis 404, and axis 406. In some illustrative examples, robotic arm 400 may be used to move wave generator 308 and detection system 310 rotationally in directions about axis 402, axis 404, and axis 406.

Figure 5:
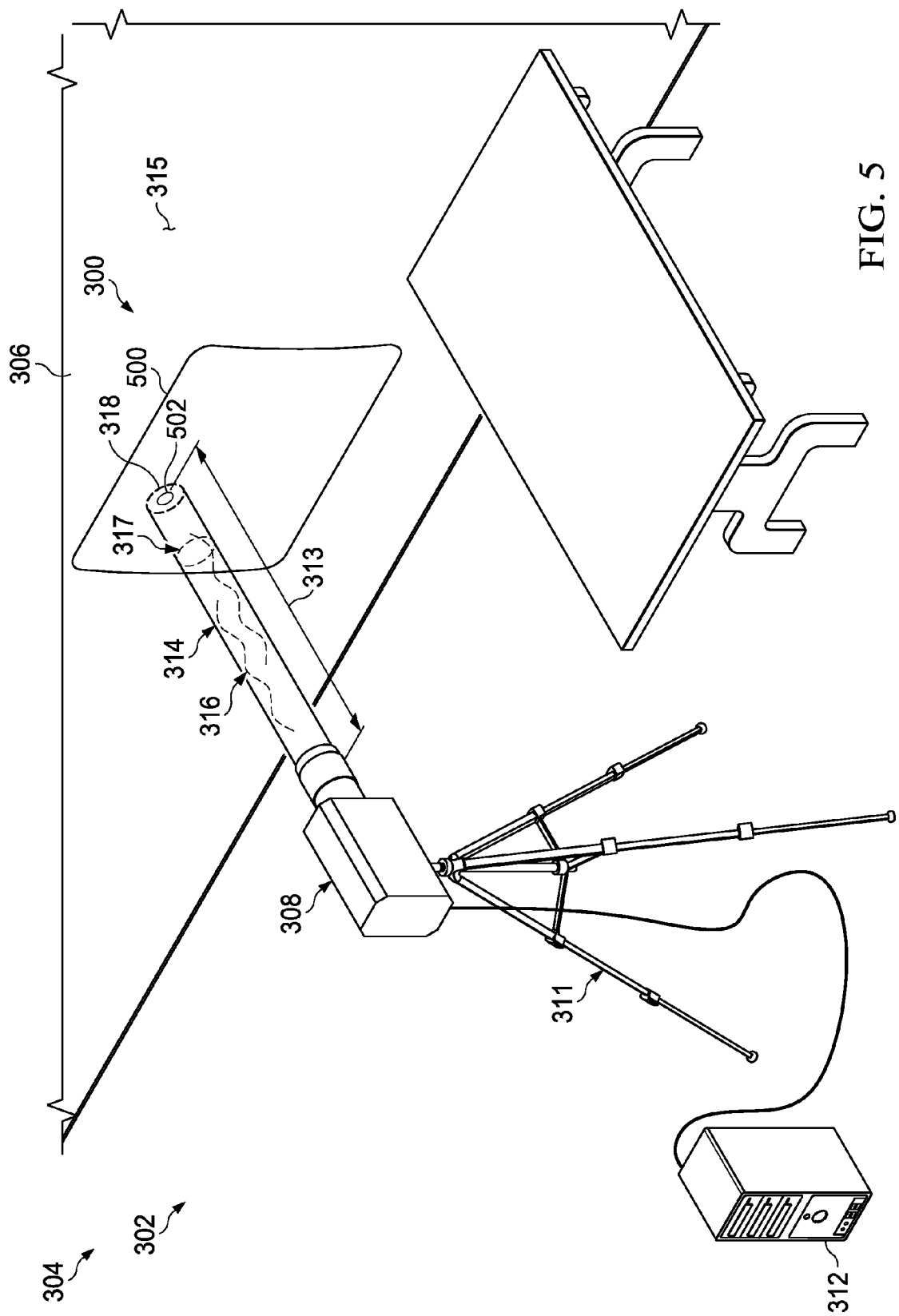
FIG. 5 is an illustration of a different type of detection system being used with a nondestructive inspection system in accordance with an illustrative embodiment.

With reference now to FIG. 5, an illustration of a different type of detection system being used with nondestructive inspection system 302 from FIG. 3 is depicted in accordance with an illustrative embodiment. In this illustrative example, thermographic film 500 is used instead of detection system 310 in FIG. 3. Thermographic film 500 may be an example of one implementation for thermographic film 214 in FIG. 2.

As depicted, thermographic film 500 is positioned over surface 315 of portion 318 of fuselage 306. Thermographic film 500 detects the heat generated by the amplified vibration of undesired feature 320 and visually presents thermographic image 502 of undesired feature 320. Thermographic image 502 includes an outline of undesired feature 320.

The illustrations of inspection environment 300 in FIGS. 3-5 are not meant to imply physical or architectural limitations to the manner in which an illustrative embodiment may be implemented. Other components in addition to or in place of the ones illustrated may be used. Some components may be optional.

The different components shown in FIGS. 3-5 may be illustrative examples of how components shown in block form in FIGS. 1-2 can be implemented as physical structures. Additionally, some of the components in FIGS. 3-5 may be combined with components in FIGS. 1-2, used with components in FIGS. 1-2, or a combination of the two.

Figure 6:
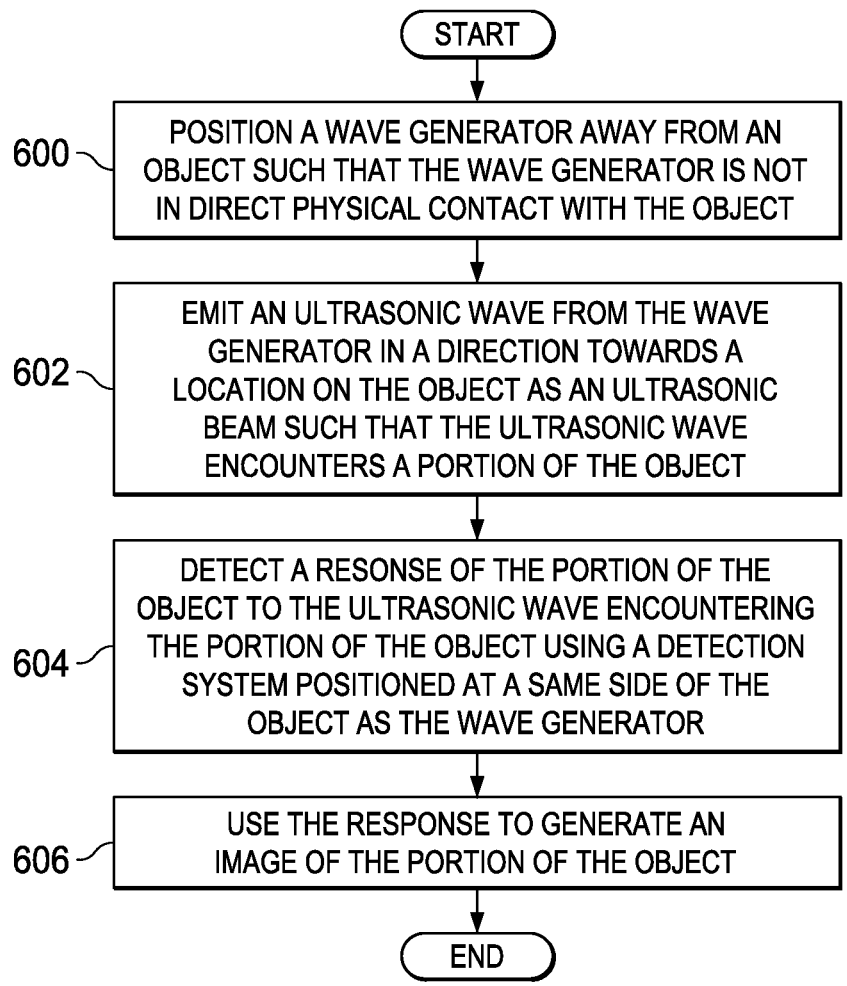
FIG. 6 is an illustration of a process for inspecting an object in the form of a flowchart in accordance with an illustrative embodiment.

With reference now to FIG. 6, an illustration of a process for inspecting an object is depicted in the form of a flowchart in accordance with an illustrative embodiment. The process illustrated in FIG. 6 may be implemented using nondestructive inspection system 106 in FIG. 1.

The process may begin by positioning a wave generator away from an object such that the wave generator is not in direct physical contact with the object (operation 600). Next, an ultrasonic wave is emitted from the wave generator in a direction towards a location on the object as an ultrasonic beam such that the ultrasonic wave encounters a portion of the object (operation 602). This portion may be a section of the object, a piece of the object, a part of the object, depending on the implementation. In operation 602, the ultrasonic wave may take the form of a hypersonic wave having a frequency, for example, without limitation, between about 1 kilohertz and about 500 kilohertz.

Thereafter, a response of the portion of the object to the ultrasonic wave encountering the portion of the object is detected using a detection system positioned at a same side of the object as the wave generator (operation 604). In operation 606, when a feature of interest is present within the portion of the object, a feature response of the feature within the portion of the object to the ultrasonic wave encountering the portion of the object may be detected using the detection system.

The response may then be used to generate an image of the portion of the object (operation 606), with the process terminating thereafter. Operation 606 may be performed in a number of different ways using detection system 110 in FIGS. 1-2. The image generated in operation 606 may be used to determine whether a feature of interest is present within the portion of the object. For example, when a feature of interest, such as an undesired feature, is present within the portion of the object, the image generated in operation 606 may provide a visual outline of the undesired feature.

Figure 7:
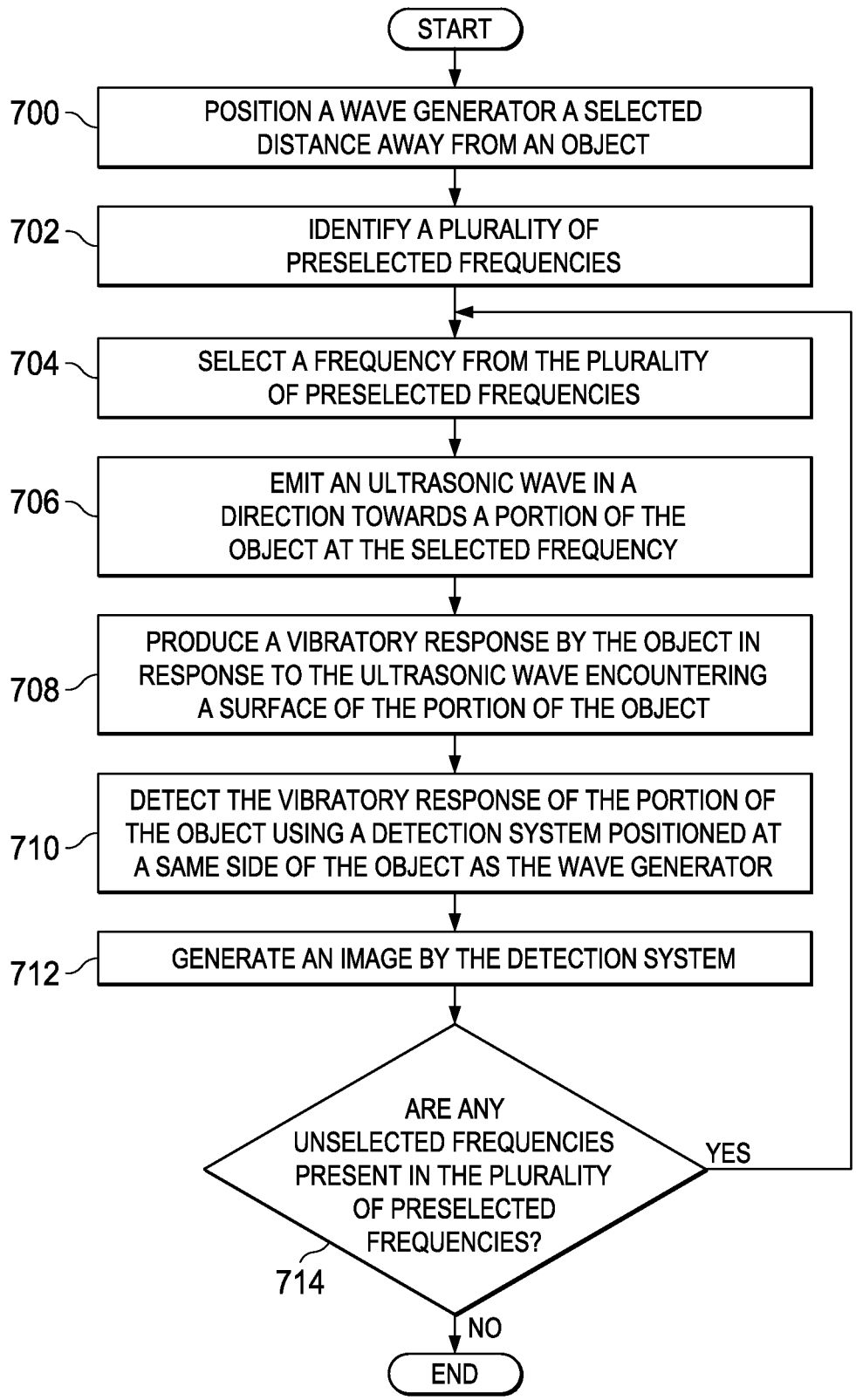
FIG. 7 is an illustration of a process for inspecting an object in the form of a flowchart in accordance with an illustrative embodiment.

With reference now to FIG. 7, an illustration of a process for inspecting an object is depicted in the form of a flowchart in accordance with an illustrative embodiment. The process illustrated in FIG. 7 may be implemented using nondestructive inspection system 106 in FIG. 1.

The process begins by positioning a wave generator a selected distance away from an object (operation 700). Next, a plurality of preselected frequencies is identified (operation 702). A frequency from the plurality of preselected frequencies is selected (operation 704).

Next, the wave generator emits an ultrasonic wave in a direction towards a portion of the object at the selected frequency (operation 706). In operation 706, the ultrasonic wave is a hypersonic wave.

A vibratory response is produced by the object in response to the ultrasonic wave encountering a surface of the portion of the object (operation 708). In other words, in operation 708, when the ultrasonic wave impinges upon the surface of the portion of the object, the object vibrates.

The vibratory response of the portion of the object is detected using a detection system positioned at a same side of the object as the wave generator (operation 710). Depending on the selected frequency, a feature present in the portion of the object may or may not have an amplified vibratory response.

An image is then generated by the detection system (operation 712). When the feature is present and has an amplified vibratory response, this image may include a visual representation of the feature.

The process then determines whether any unselected frequencies are present in the plurality of preselected frequencies (operation 714). If no unselected frequencies are present, the process terminates. Otherwise, the process returns to operation 704 as described above. Thus, the process of emitting the ultrasonic wave from the wave generator may be repeated a number of times such that a plurality of ultrasonic waves is emitted at a plurality of preselected frequencies. In this manner, a frequency sweep of the portion of the object may be performed to determine whether the feature is present in the portion of the object.

The overall process described in FIG. 7 may be repeated any number of times such that any number of portions of the object may be inspected. For example, the wave generator may be repositioned such that another ultrasonic wave generated by the wave generator is directed towards another portion of the object. The repositioning of the wave generator may include translating the wave generator, rotating the wave generator, or both. In this manner, different portions of the object may be quickly and easily inspected at subsequent times.

Figure 8:
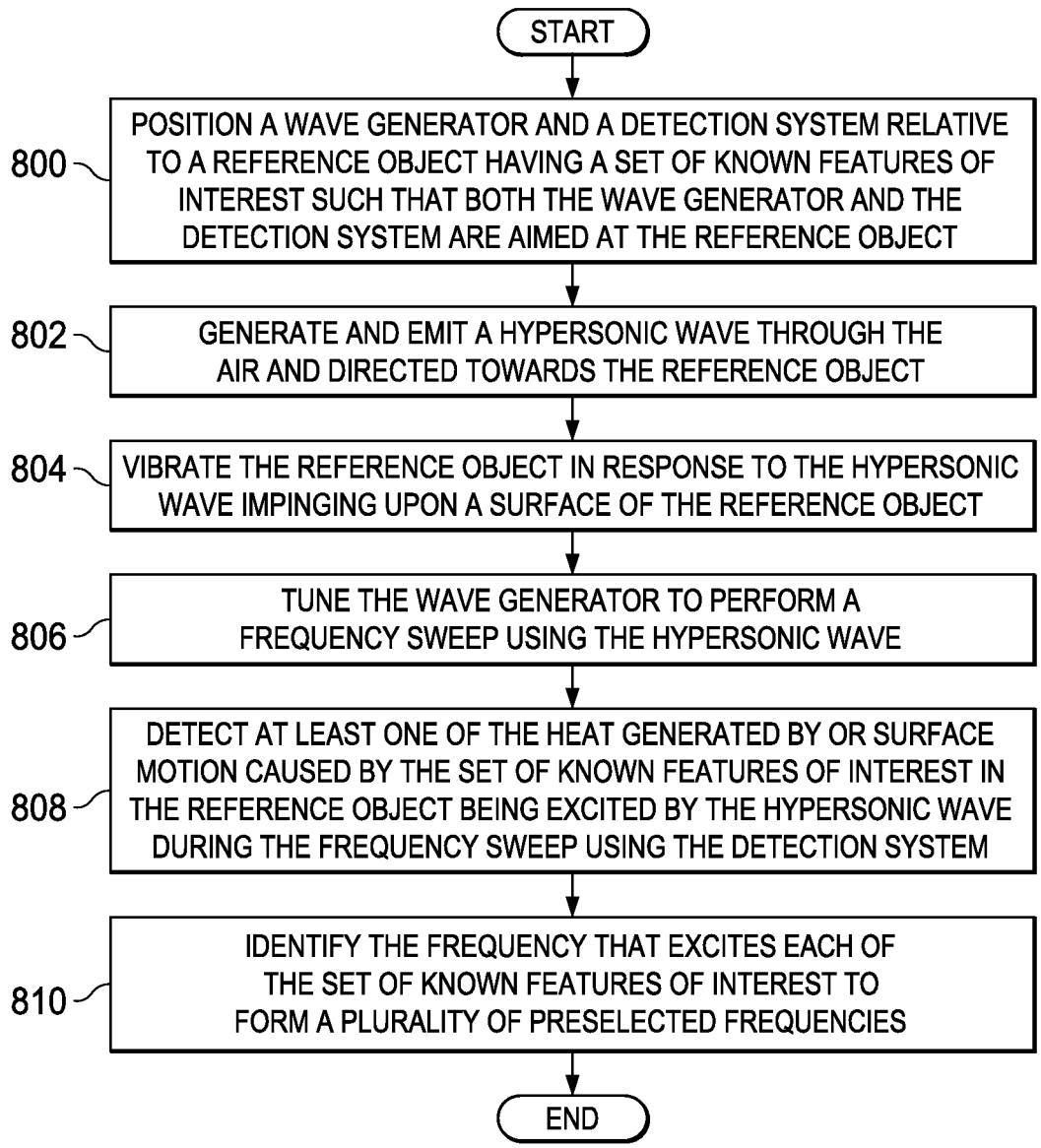
FIG. 8 is an illustration of a process for identifying a plurality of preselected frequencies in the form of a flowchart in accordance with an illustrative embodiment.

With reference now to FIG. 8, an illustration of a process for identifying a plurality of preselected frequencies is depicted in the form of a flowchart in accordance with an illustrative embodiment. The process illustrated in FIG. 8 may be implemented using nondestructive inspection system 106 in FIG. 1.

The process begins by positioning a wave generator and a detection system relative to a reference object having a set of known features of interest such that both the wave generator and the detection system are aimed at the reference object (operation 800). Operation 800 may be performed by a human operator positioning the wave generator or a robotic device, such as robotic device 117 in FIG. 1, positioning the wave generator. The reference object in operation 800 may also be referred to as a standard.

The set of known features of interest in the reference object may include one or more features, each one distinguishable from the rest. For example, each known feature of interest may have at least one of a different type, size, property, or other characteristic compared to the rest of the set of known features of interest.

The reference object may also be referred as a standard in some cases. The reference object may be substantially equivalent to an object that will be inspected at a later time with respect to at least one of type, size, shape, thickness, or one or more other properties. The set of known features of interest may represent the one or more types of features of interest for which the object may be inspected.

In one illustrative example, each of the set of known features in the reference object may be in a different location in the reference object. In other illustrative examples, one or more of the set of known features of interest may overlap or be co-located in the reference object.

The wave generator then generates and emits a hypersonic wave through the air and directed towards the reference object (operation 802). The reference object is vibrated in response to the hypersonic wave impinging upon a surface of the reference object (operation 804).

Next, the wave generator may be tuned to perform a frequency sweep using the hypersonic wave (operation 806). In one illustrative example, operation 806 may be performed by emitting the hypersonic wave at every frequency at a selected interval within a frequency range. For example, the selected interval may be about one kilohertz, about two kilohertz, about five kilohertz, or some other frequency internal.

At least one of heat generated by or surface motion caused by the set of known features of interest in the reference object being excited by the hypersonic wave during the frequency sweep is detected using the detection system (operation 808). For example, in operation 808, a thermographic imaging system, such as thermographic imaging system 200 in FIG. 2, may be used to detect the heat generated by the set of known features of interest vibrating in an amplified manner relative to a rest of the reference object. In another example, an interferometry system or a motion magnification system may be used to image the surface motion across each of the set of known features caused by each feature of interest vibrating in an amplified manner relative to a rest of the reference object.

Thereafter, a frequency that excites each of the set of known features of interest is identified to form a plurality of preselected frequencies (operation 810), with the process terminating thereafter. This plurality of preselected frequencies may then be used to perform nondestructive inspection of objects.

In one illustrative example, each of the set of known features of interest may produce a feature response at a different frequency due to the differences between the different known features of interest. In operation 810, the frequency at which a particular known feature of interest produces the feature response may be preselected for use in later inspection. In particular, this preselected frequency may be used to inspect an object to determine whether a feature substantially equivalent to or similar to the particular known feature of interest is present within the object.

Figure 9:
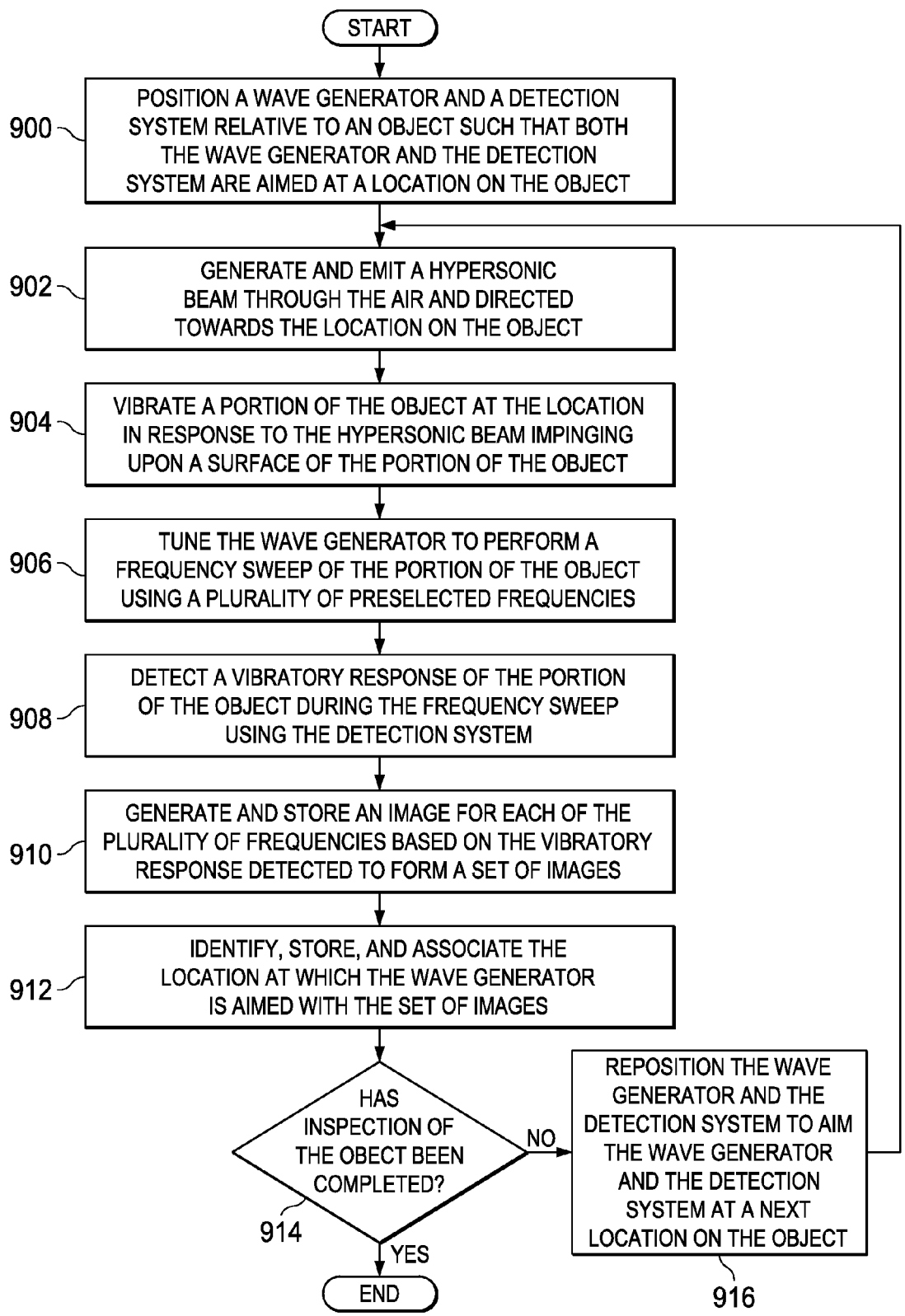
FIG. 9 is an illustration of a process for inspecting an object in the form of a flowchart in accordance with an illustrative embodiment.

With reference now to FIG. 9, an illustration of a process for inspecting an object is depicted in the form of a flowchart in accordance with an illustrative embodiment. The process illustrated in FIG. 9 may be performed using nondestructive inspection system 106 in FIG. 1.

The process begins by positioning a wave generator and a detection system relative to an object such that both the wave generator and the detection system are aimed at a location on the object (operation 900). Operation 900 may be performed by a human operator positioning the wave generator or an automated device, such as robotic device 117 in FIG. 1, positioning the wave generator.

The wave generator then generates and emits a hypersonic beam through the air and directed towards the location on the object (operation 902). A portion of the object at the location may vibrate in response to the hypersonic beam impinging upon a surface of the portion of the object (operation 904).

Next, the wave generator is tuned to perform a frequency sweep of the portion of the object using a plurality of preselected frequencies (operation 906). In operation 906, the plurality of preselected frequencies used may be the plurality of preselected frequencies identified by the process described in FIG. 8. As described above, the plurality of preselected frequencies identified in operation 810 in FIG. 8 may be the frequencies at which a set of known features of interest are known to produce feature responses. The frequency sweep is performed in operation 908 such that the object may be inspected to determine whether any of the set of known features of interest are present within the object.

A vibratory response of the portion of the object during the frequency sweep is detected using the detection system (operation 908). The vibratory response detected in operation 908 may include zero, one or more feature responses. For example, when a feature is present within the portion of the object, a corresponding feature response may be included in the vibratory response detected in operation 908 when the hypersonic beam causes amplified vibration of the feature relative to a rest of the portion of the object.

The amplified vibration of the feature may be caused when, for example, without limitation, one of the plurality of preselected frequencies for the hypersonic beam contacting the surface of the portion of the object is within a selected range of the natural frequency of the feature. A feature response may be detected as heat or surface motion resulting from the amplified vibration of the feature.

An image is generated and stored for each of the plurality of frequencies based on the vibratory response detected to form a set of images (operation 910). The location at which the wave generator is aimed is identified, stored, and associated with the set of images (operation 912). Operation 912 may be performed using a positioning system, such as positioning system 148 in FIG. 1, and a location identifier, such as location identifier 150 in FIG. 1.

Thereafter, a determination is made as to whether inspection of the object has been completed (operation 914). If the inspection of the object has been completed, the process terminates. Otherwise, the process repositions the wave generator and the detection system to aim the wave generator and the detection system at a next location on the object (operation 916), with the process then returning to operation 902 as described above.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, a segment, a function, a portion of an operation or step, some combination thereof.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 10:
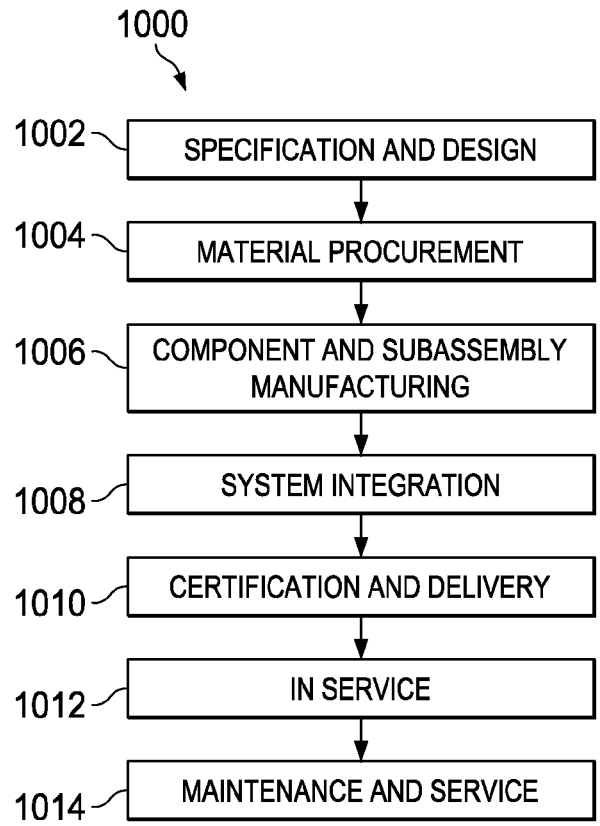
FIG. 10 is an illustration of an aircraft manufacturing and service method in the form of a block diagram in accordance with an illustrative embodiment.
Figure 11:
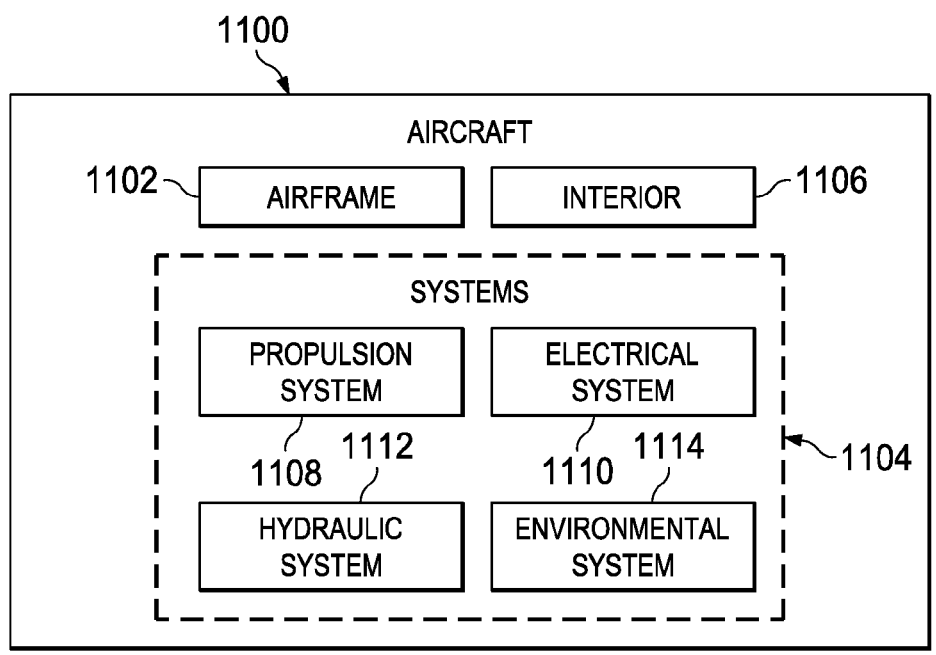
FIG. 11 is an illustration of an aircraft in the form of a block diagram in which an illustrative embodiment may be implemented.

The illustrative embodiments of the disclosure may be described in the context of aircraft manufacturing and service method 1000 as shown in FIG. 10 and aircraft 1100 as shown in FIG. 11. Turning first to FIG. 10, an illustration of an aircraft manufacturing and service method is depicted in the form of a block diagram in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by at least one of a system integrator, a third party, or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of an aircraft is depicted in the form of a block diagram in which an illustrative embodiment may be implemented. In this example, aircraft 1100 is produced by aircraft manufacturing and service method 1000 in FIG. 10 and may include airframe 1102 with plurality of systems 1104 and interior 1106. Examples of systems 1104 include one or more of propulsion system 1108, electrical system 1110, hydraulic system 1112, and environmental system 1114. Any number of other systems may be included. Although an aerospace example is shown, different illustrative embodiments may be applied to other industries, such as the automotive industry.

The apparatuses and methods embodied herein may be employed during at least one of the stages of aircraft manufacturing and service method 1000 in FIG. 10. In particular, nondestructive inspection system 106 from FIG. 1 may be used to inspect a structure of aircraft 1100 during any one of the stages of aircraft manufacturing and service method 1000. For example, without limitation, nondestructive inspection system 106 from FIG. 1 may be used inspect one or more aircraft structures during at least one of component and subassembly manufacturing 1006, system integration 1008, certification and delivery 1010, in service 1012, routine maintenance and service 1014, or some other stage of aircraft manufacturing and service method 1000. Still further, nondestructive inspection system 106 from FIG. 1 may be used to inspect airframe 1102, interior 1106, or any one of plurality of systems 1104 of aircraft 1100.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10. One or more apparatus embodiments, method embodiments, or a combination thereof may be utilized while aircraft 1100 is in service 1012, during maintenance and service 1014 in FIG. 10, or both. The use of a number of the different illustrative embodiments may substantially expedite the assembly of and reduce the cost of aircraft 1100.

Thus, the illustrative embodiments provide a method and apparatus for inspecting objects from a distance. Nondestructive inspection system 106 in FIG. 1 may allow inspections to be performed quickly and without physically impacting objects in an undesired manner. Further, nondestructive inspection system 106 may allow visual representations of features to be generated with a desired level of accuracy.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. An apparatus comprising:
a wave generator positioned away from an object, wherein the wave generator emits an ultrasonic wave in a direction towards a location on the object such that the ultrasonic wave encounters a portion of the object;
a detection system positioned at a same side of the object as the wave generator, wherein the detection system detects a feature response of a feature within the portion of the object to the ultrasonic wave encountering the portion of the object; and wherein:
the feature response is a portion of a response that is different from a rest of the response and corresponds to an amplified vibration of the feature relative to a rest of the portion of the object in response to the ultrasonic wave encountering the portion of the object; and
the detection system is configured to detect the amplified vibration of the feature using at least one of a thermographic imaging system configured to detect heat generated by the amplified vibration, an infrared thermographic imaging system configured to detect infrared radiation generated by the amplified vibration, an imaging system configured to detect and magnify surface motion produced by the amplified vibration, an optical interferometry system, an electronic speckle pattern interferometry system, or a shearography system.

2. The apparatus of claim 1, wherein the thermographic imaging system is an infrared thermographic imaging system that detects infrared radiation generated by the amplified vibration of the feature and generates an image of the feature based on the infrared radiation detected.

3. The apparatus of claim 1, wherein the thermographic imaging system comprises:
a thermographic material that is positioned relative to a surface of the portion of the object, wherein the thermographic material generates a visual representation of the feature on a portion of the thermographic material in response to detecting the heat generated by the amplified vibration of the feature.

4. The apparatus of claim 1 further comprising:
a location identifier that identifies a location of the feature with respect to a coordinate system for the object.

5. The apparatus of claim 1 further comprising:
a controller that controls an operation of the wave generator such that the wave generator emits the ultrasonic wave that is a hypersonic wave having a frequency between about 1 kilohertz and about 500 kilohertz.

6. The apparatus of claim 1, wherein the ultrasonic wave emitted by the wave generator is one of a plurality of ultrasonic waves emitted by the wave generator and wherein the wave generator emits the plurality of ultrasonic waves having a plurality of preselected frequencies.

7. The apparatus of claim 1, wherein the wave generator is positioned at least two inches away from a surface of the portion of the object.

8. The apparatus of claim 1, wherein the ultrasonic wave is directed at the location on the object as an ultrasonic beam having a substantially constant cross-sectional shape.

9. The apparatus of claim 1, wherein the ultrasonic wave travels through a number of fluids over a selected distance until the ultrasonic wave encounters a surface of the portion of the object.

10. The apparatus of claim 1 further comprising:
a device that positions the wave generator such that the ultrasonic wave is emitted in the direction towards the location on the object.

11. The apparatus of claim 10, wherein the device is a hypersonic wave generator.

12. The apparatus of claim 1, wherein the detection system is configured to detect the amplified vibration of the feature using the thermographic imaging system.

13. The apparatus of claim 1, wherein the detection system is configured to detect the amplified vibration of the feature using the infrared thermographic imaging system.

14. The apparatus of claim 1, wherein the detection system is configured to detect the amplified vibration of the feature using the imaging system.

15. The apparatus of claim 1, wherein the detection system is configured to detect the amplified vibration of the feature using the optical interferometry system.

16. A method for inspecting an object, the method comprising:
positioning a wave generator away from the object;
emitting an ultrasonic wave from the wave generator in a direction towards a location on the object such that the ultrasonic wave encounters a portion of the object; and
detecting a feature response of a feature within the portion of the object to the ultrasonic wave encountering the portion of the object using a detection system positioned at a same side of the object as the wave generator, and wherein detecting further comprises distinguishing the feature response from a response of a rest of the portion of the object, wherein the feature response is produced when the feature within the portion of the object has an amplified vibration relative to the rest of the portion of the object in response to the ultrasonic wave encountering the portion of the object.

17. The method of claim 16, wherein detecting the feature response comprises:
detecting the amplified vibration of an undesired feature using at least one of a thermographic imaging system configured to detect heat generated by the amplified vibration, an infrared thermographic imaging system configured to detect infrared radiation generated by the amplified vibration, an imaging system configured to detect and magnify surface motion produced by the amplified vibration, an optical interferometry system, an electronic speckle pattern interferometry system, and a shearography system.

18. The method of claim 16, further comprising:
generating an image of the feature in response to detecting the feature response.

19. The method of claim 16, wherein emitting the ultrasonic wave from the wave generator comprises:
emitting an ultrasonic beam comprising the ultrasonic wave at a frequency between about 1 kilohertz and about 500 kilohertz from the wave generator, wherein the ultrasonic wave has a substantially constant cross-sectional shape.

20. The method of claim 16 further comprising:
repeating the step of emitting the ultrasonic wave from the wave generator a number of times such that a plurality of ultrasonic waves is emitted at a plurality of preselected frequencies.

* * * * *